(12) United States Patent
Favero et al.

(10) Patent No.: US 11,802,109 B2
(45) Date of Patent: Oct. 31, 2023

(54) METHOD FOR THE PURIFICATION OF ACRYLAMIDO-2-METHYL-2-PROPANESULPHONIC ACID

(71) Applicant: SNF GROUP, Andrezieux Boutheon (FR)

(72) Inventors: Cédrick Favero, Andrezieux Boutheon (FR); Johann Kieffer, Andrezieux Boutheon (FR); Benoît Legras, Andrezieux Boutheon (FR); Raphaël Doudin, Andrezieux Boutheon (FR)

(73) Assignee: SNF GROUP, Andrezieux Boutheon (FR)

( * ) Notice: Subject to any disclaimer, the term of this patent is extended or adjusted under 35 U.S.C. 154(b) by 156 days.

(21) Appl. No.: 17/447,754

(22) Filed: Sep. 15, 2021

(65) Prior Publication Data

US 2022/0089530 A1     Mar. 24, 2022

(30) Foreign Application Priority Data

Sep. 18, 2020 (FR) ...................................... 2009493

(51) Int. Cl.
| | |
|---|---|
| C07C 303/44 | (2006.01) |
| C08F 20/58 | (2006.01) |
| C02F 1/56 | (2023.01) |
| C02F 1/54 | (2023.01) |
| C02F 1/52 | (2023.01) |

(52) U.S. Cl.
CPC .......... *C07C 303/44* (2013.01); *C02F 1/5272* (2013.01); *C02F 1/56* (2013.01); *C08F 20/58* (2013.01)

(58) Field of Classification Search
CPC ........ C07C 303/44; C02F 1/5272; C02F 1/53; C08F 20/58
See application file for complete search history.

(56) References Cited

U.S. PATENT DOCUMENTS

| | | | |
|---|---|---|---|
| 4,219,498 A * | 8/1980 | Doi .................. | C07C 309/15 562/105 |
| 4,337,215 A | 6/1982 | Doi et al. | |
| 6,448,347 B1 | 9/2002 | Quinn et al. | |
| 2010/0274048 A1 | 10/2010 | Wakayama | |
| 2020/0031765 A1 | 1/2020 | Favero et al. | |

FOREIGN PATENT DOCUMENTS

| | | |
|---|---|---|
| CN | 102351744 A | 2/2012 |
| CN | 103664709 A | 3/2014 |
| FR | 3064004 A1 | 9/2018 |
| WO | 2009072480 A1 | 12/2008 |

OTHER PUBLICATIONS

French Search Report for FR 2009493 dated Jun. 1, 2021.

* cited by examiner

*Primary Examiner* — Robert D Harlan
(74) *Attorney, Agent, or Firm* — Heslin Rothenberg Farley & Mesiti P.C.

(57) ABSTRACT

The invention relates to a method for the purification of acrylamido-2-methyl-2-propanesulphonic acid comprising the following successive steps:

1) preparation of a suspension of acrylamido-2-methyl-2-propanesulphonic acid crystals by distillation of an aqueous solution of acrylamido-2-methyl-2-propanesulphonic acid in order to obtain a suspension of acrylamido-2-methyl-2-propanesulphonic acid crystals, 2) isolation of the acrylamido-2-methyl-2-propanesulphonic acid crystals generally by solid/liquid separation from said suspension in order to isolate said acrylamido-2-methyl-2-propanesulphonic acid crystals, characterised in that the distillation step is carried out continuously and at a pressure below atmospheric pressure.

The invention also relates to a polymer obtained from acrylamido-2-methyl-2-propanesulphonic acid crystals or its salts, obtained according to such a method, and to the use of said polymer in oil and gas recovery, in water treatment, in sludge treatment, in manufacturing paper, in construction, in mining, in cosmetic formulation, in detergent formulation, in textile making, or in agriculture.

18 Claims, 1 Drawing Sheet

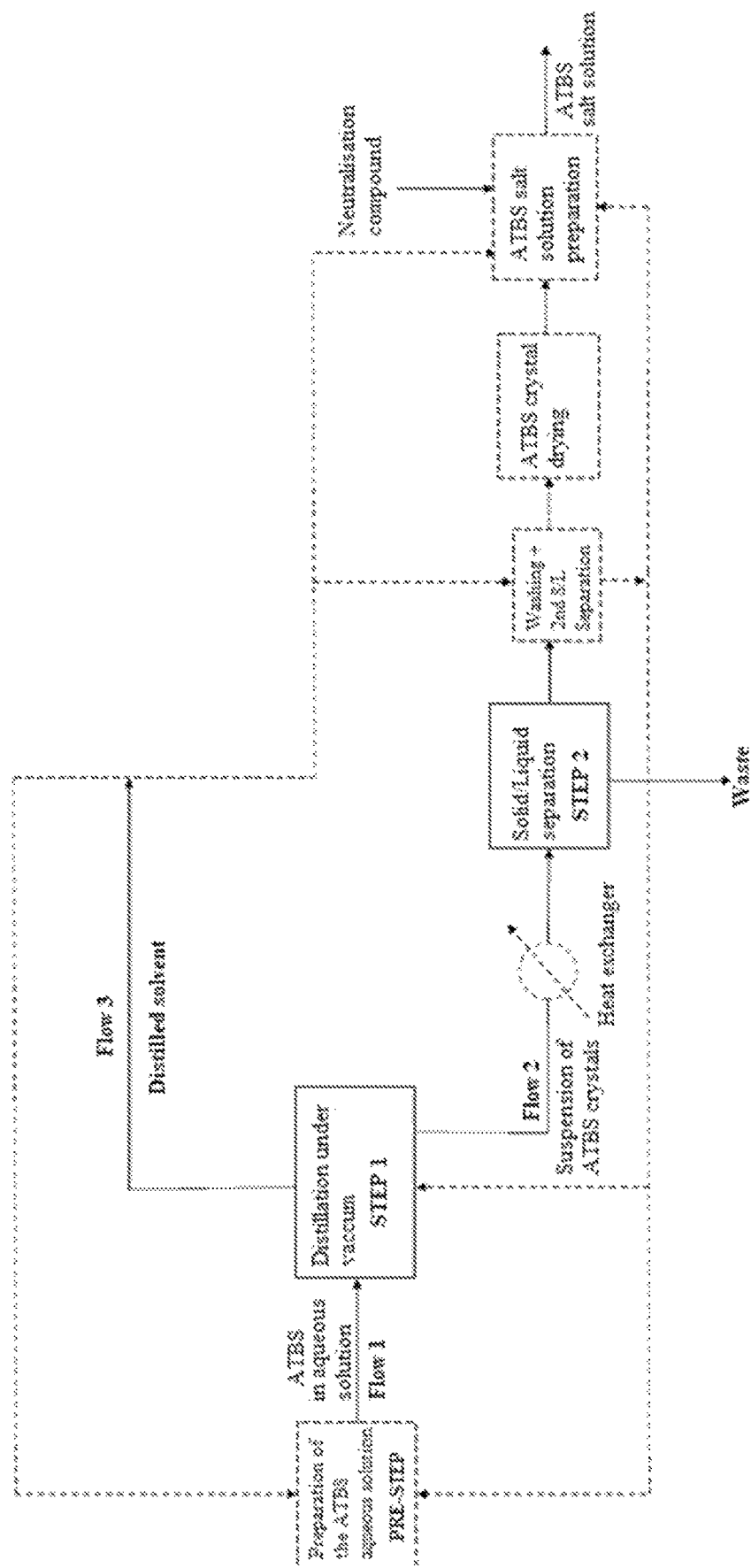

METHOD FOR THE PURIFICATION OF ACRYLAMIDO-2-METHYL-2-PROPANESULPHONIC ACID

CROSS REFERENCE TO RELATED APPLICATIONS

This application claims priority to French Patent Application No. 2009493 filed on Sep. 18, 2020, the entire contents of which are hereby incorporated by reference herein.

TECHNICAL FIELD OF THE INVENTION

The present invention relates to a method for the purification of acrylamido-2-methyl-2-propanesulphonic acid (ATBS) by continuous distillation.

BACKGROUND

Acrylamido-2-methyl-2-propanesulfonic acid, also known as ATBS, is an acrylic monomer with a sulphonic acid function having the formula:

[Chem. 1]

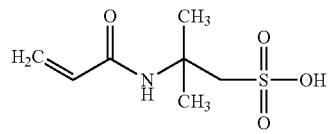

It is widely used as an additive in acrylic fibres, or alternatively as a starting material for obtaining polymers used as dispersants, thickeners, flocculants or superabsorbents in various sectors such as the petroleum industry, construction, textiles, water treatment (desalination of seawater, mineral industry, etc.) or cosmetics.

The reaction carried out in the method for the preparation of acrylamido-2-methyl-2-propanesulphonic acid corresponds to the reaction scheme below, in which acrylonitrile is present in excess so as to be both the solvent of the reaction and a reagent. The acrylonitrile is brought into contact with fuming sulphuric acid (oleum) and isobutylene.

[Chem. 2]

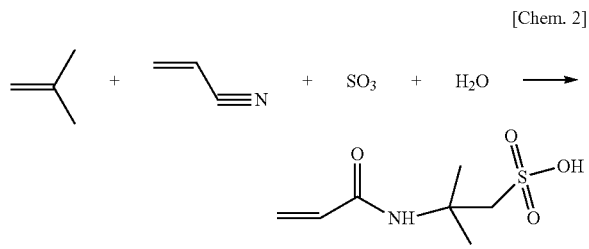

Acrylamido-2-methyl-2-propanesulphonic acid is not soluble in the acrylonitrile solvent. As a result, the reaction product is in the form of a suspension of crystals in the reaction solvent.

As examples, documents U.S. Pat. No. 6,448,347 and CN 102351744 describe a method for the production of acrylamido-2-methyl-2-propanesulphonic acid according to a continuous mode.

The acrylamido-2-methyl-2-propanesulphonic acid is subsequently separated from the acrylonitrile, generally by filtration, and then dried. Drying of the acrylamido-2-methyl-2-propanesulphonic acid is necessary in order to reduce the amount of acrylonitrile and acrylamide remaining in the crystal. In fact, since these two compounds are classified as CMR carcinogenic components, it is necessary to carry out effective filtration followed by drying, in order to obtain the lowest possible contents of these two compounds.

Very often, an additional purification step is necessary because impurities, even at low concentrations, greatly affect the polymerisation, as well as the quality of the polymer obtained, more specifically its molecular weight and the level of water insoluble matter.

Thus, document WO 2009/072480, which relates to a method for the production of acrylamido-2-methyl-2-propanesulphonic acid, explains that impurities of the 2-methyl-2-propenylsulphonic acid (IBSA) and 2-methylidene-1,3-propylenedisulphonic acid (IBDSA) type strongly affect the polymerisation beyond a certain concentration.

There are numerous methods for the purification of acrylamido-2-methyl-2-propanesulphonic acid. In most cases, the acrylamido-2-methyl-2-propanesulphonic acid is redissolved in a hot solvent in order to obtain a saturated solution. During cooling, high-purity crystals are obtained.

The crystals thus obtained are then dried under vacuum in order to further improve their purity by eliminating the residual solvent.

Document U.S. Pat. No. 4,337,215 describes a method for the purification of acrylamido-2-methyl-2-propanesulphonic acid by recrystallisation from acetic acid, by hot dissolution and crystallisation by a cooling ramp. Despite the good purity of the 2-acrylamido-2-methylpropanesulphonic acid obtained, the method, the yield of which is limited, involves multiple dissolution/cooling steps and requires a treatment of the acetic acid used to regenerate it by distillation before reuse in a new batch for the recrystallisation of 2-acrylamido-2-methylpropanesulphonic acid. The method described is of the "batch" type, i.e. in discontinuous mode.

Document CN 103664709 describes a method for the preparation of acrylamido-2-methyl-2-propanesulphonic acid which makes it possible to dispense with this long and expensive drying step. The drying step is replaced by a step for washing with glacial acetic acid in which the ATBS is not soluble. Although this method makes it possible to shorten the duration of the synthesis of acrylamido-2-methyl-2-propanesulphonic acid, the solvent consumption and the thermal energy required for the purification by recrystallisation are still too great. The method described is of the "batch" type.

All these methods use a saturated solution of acrylamido-2-methyl-2-propanesulphonic acid dissolved in a solvent requiring a step of dissolving the crystals when hot, which adds a highly energy-consuming step and poses various problems related to the use of solvent (risk during handling, transport and storage of the solvent, degradation of the equipment used related to the nature of the solvent, environmental footprint).

In the current context, there is a need to develop new processes that comply with QHSE (Quality, Health, Safety and Environment) standards.

The Quality, Health, Safety, Environment (QHSE) policy is an area of expertise including the identification and compliance with the production standards of a company, with particular attention to the working environment of employees, equipment and respect for the environment:

Quality: Maintenance of good quality of products offered.

Health and Safety: Reduced risks for employees and facilities.

Environment: Greener methods with a reduced environmental impact.

The applicant has discovered, unexpectedly, that the problems described above can be solved by means of a method for the purification of acrylamido-2-methyl-2-propanesulphonic acid carried out continuously by distillation of an aqueous solution of acrylamido-2-methyl-2-propanesulphonic acid at reduced pressure.

An aim of the present invention is to provide a novel method for the purification of acrylamido-2-methyl-2-propanesulphonic acid meeting the QHSE expectations.

The method according to the invention makes it possible to obtain acid crystals of very good quality, while reducing the risks associated with the handling of toxic solvents and reducing the environmental impact of the method for the purification of acrylamido-2-methyl-2-propanesulphonic acid.

DISCLOSURE OF THE INVENTION

The present invention relates to a method for the purification of acrylamido-2-methyl-2-propanesulphonic acid by continuous distillation.

The present invention also relates to a method for the production of 2-acrylamido-2-methylpropanesulphonic acid (ATBS) comprising a step of purification of said acrylamido-2-methyl-2-propanesulphonic acid by the method according to the invention.

The present invention further relates to the use of the crystals of acrylamido-2-methyl-2-propanesulphonic acid obtained according to the method of the invention for the preparation of a salt or a solution of salts of acrylamido-2-methyl-2-propanesulphonic acid.

The present invention also relates to the use of the crystals of acrylamido-2-methyl-2-propanesulphonic acid obtained according to the method of the invention, for the production of polymers.

Finally, the invention also relates to the polymers obtained from acrylamido-2-methyl-2-propanesulphonic acid or its salts, obtained from crystals of acrylamido-2-methyl-2-propanesulphonic acid or its salts obtained according to the method of the invention, as well as to the use of these polymers in the recovery of oil and gas, in the treatment of water, in the treatment of sludge, in the manufacture of paper, in construction, in the mining industry, in the formulation of cosmetic products, in the formulation of detergents, in the manufacture of textiles, or in agriculture.

The method according to the invention may be incorporated in all the methods for the preparation of acrylamido-2-methyl-2-propanesulphonic acid which already exist.

Method for the Purification of acrylamido-2-methyl-2-propanesulphonic Acid

The present invention aims for a method for the purification of acrylamido-2-methyl-2-propanesulphonic acid comprising the following successive steps:

1) preparation of a suspension of acrylamido-2-methyl-2-propanesulphonic acid crystals by distillation of an aqueous solution of acrylamido-2-methyl-2-propanesulphonic acid, 2) isolation of the acrylamido-2-methyl-2-propanesulphonic acid crystals by solid/liquid separation from said suspension, characterised in that the distillation step is carried out continuously and at a pressure below atmospheric pressure.

As its name indicates, the purified acrylamido-2-methyl-2-propanesulphonic acid according to the invention is in acid form.

The term "successive steps" designates steps that follow each other chronologically. In other words, successive steps are carried out in the order indicated and cannot be interchanged. On the other hand, one or more intermediate steps may optionally be interposed between two successive steps.

The term "aqueous solution" is understood to mean a water-based solution which, in general, does not comprise solid particles of acrylamido-2-methyl-2-propanesulphonic acid. Nevertheless, it is possible that a small quantity of solid particles of acrylamido-2-methyl-2-propanesulphonic acid is present in the said solution. The term "small quantity" is understood to mean less than 5%, preferably less than 2%, still more preferably less than 1% relative to the mass of the aqueous solution. Preferably, the solution of acrylamido-2-methyl-2-propanesulphonic acid does not contain any solid particles of acrylamido-2-methyl-2-propanesulphonic acid.

In general, the limits of the ranges of values indicated below may be combined according to the invention. Thus, two value ranges defined by a single terminal also define the value range delimited by these two terminals.

BRIEF DESCRIPTION OF THE FIGURE

FIG. 1 is a schematic view of the method according to the invention (solid line), with its different variants (dotted line).

Of course, the dimensions and the proportions of the elements illustrated in FIG. 1 have had to be exaggerated compared with reality; this has been carried out with the sole aim of facilitating the understanding of the invention.

DETAILED DESCRIPTION

FIG. 1 shows the steps of the method according to the invention, in solid lines for the mandatory steps, and in dotted lines for the optional steps. The flows of fluids are represented in the same way, i.e. either in solid lines or in dotted lines.

According to the method of the invention, a flow 1 of ATBS in aqueous solution is treated in step 1), generally by a distillation device. This aqueous solution is either obtained from an optional pre-step for the preparation of an aqueous solution of ATBS, or provided as such. A flow 2 of a suspension of ATBS crystal, and a flow 3 of distilled solvent emerge from step 1). The solid/liquid separation step 2 is carried out, for example by means of a centrifuge or a closed filter of the Nutsche type.

These steps, as well as the optional steps, will be detailed below, with reference to FIG. 1.

Pre-Step—Preparation of an Aqueous Solution of acrylamido-2-methyl-2-propanesulphonic Acid (Optional)

Usually, a purification method requires the hot dissolution of the product to be purified in a solvent in order to obtain a saturated solution which, during a step of cooling the solution, promotes the formation of crystals.

In the case of acrylamido-2-methyl-2-propanesulphonic acid, the solvents conventionally used are advantageously acetic acid, acrylonitrile and, in general, all the solvents conventionally used in purifications and having from 1 to 10 carbon atoms per molecule of solvent (i.e. most often. alcohols, amides, ketones, aldehydes, ethers, carboxylic acids, alkanes, esters, nitriles, halogenated hydrocarbons, etc.), and their mixtures.

Such solvents pose different problems related to their use, whether it is the risks related to their handling, the risks during their transport and storage or the risks of degradation of the equipment used (in particular in the case of acids).

By virtue of the method according to the invention, it is possible to use mainly water as solvent in the purification of acrylamido-2-methyl-2-propanesulphonic acid.

According to a particular embodiment of the invention, the aqueous solution of acrylamido-2-methyl-2-propane sulphonic acid, prior to distillation, comprises at least 80% by mass of water, preferably at least 85% by mass, more preferably at least 90% by mass, more preferably at least 92% by mass, more preferably at least 95% by mass, and even more preferably at least 99% by mass, relative to the total mass of the solvents of the solution. Preferably, it comprises 100% by mass of water relative to the total mass of the solvents of the solution.

The aqueous solution of acrylamido-2-methyl-2-propanesulphonic acid is, for example, obtained by dissolving acrylamido-2-methyl-2-propanesulphonic acid in an aqueous solution. This dissolution may be carried out in a mixer. By way of example and in a non-limiting manner, such a mixer may be chosen from reactors with stirrers, loop reactors, static mixers, microreactors, and piston reactors.

It is possible that the aqueous solution of acrylamido-2-methyl-2-propanesulphonic acid used in the method according to the invention comprises other solvent(s). By way of example and in a non-limiting manner, this/these solvent(s) may originate from impurities present in the acrylamido-2-methyl-2-propanesulphonic acid to be purified.

Advantageously, the aqueous solution of acrylamido-2-methyl-2-propanesulphonic acid prepared contains less than 20% by weight of solvent(s) other than water, preferably less than 15% by weight, more preferably less than 10% by weight, more preferably less than 8% by weight, even more preferably less than 5% by weight, and even more preferably less than 1% by weight, relative to the total weight of the solvents of the solution. Preferably, said aqueous solution does not contain any solvent other than water.

The dissolution can be carried out hot (typically at more than 50° C.), cold (typically at less than 10° C.), or at ambient temperature, i.e. between 10° C. and 40° C., preferably between 10° C. and 30° C. Advantageously, the dissolution of the acrylamido-2-methyl-2-propanesulphonic acid takes place at ambient temperature.

The monomers of the aqueous solution of acrylamido-2-methyl-2-propanesulphonic acid are generally entirely in acid form, i.e. they are not neutralised in the form of salts of acrylamido-2-methyl-2-propanesulphonic acid. If there are salts of acrylamido-2-methyl-2-propanesulphonic acid in said aqueous solution, they are typically present at less than 1%, relative to the total of the acrylamido-2-methyl-2-propanesulphonic acid monomers of the solution.

The concentration of acrylamido-2-methyl-2-propanesulphonic acid in the aqueous solution of acrylamido-2-methyl-2-propanesulphonic acid distilled in step 1) is generally comprised between 10% by mass (relative to the mass of the aqueous solution) and the percentage leading to saturation of the solution, referred to here as saturation of the solution. Preferably, it is between 20% by mass and the saturation of the solution, more preferably between 30% by mass and the saturation of the solution. In one particular embodiment, the solution of acrylamido-2-methyl-2-propanesulphonic acid is saturated.

The saturation value of the aqueous solution of acrylamido-2-methyl-propanesulphonic acid depends on temperature. Thus, at 25° C. for example, the saturation of the solution if 58% by mass. A person skilled in the art will be able to adjust the concentration of the solution of acrylamido-2-methyl-2-propanesulphonic acid as a function of the temperature in order to arrive at a saturated solution.

The method according to the invention also operates with a solution of which the concentration is low, that is to say less than 10% by mass of ATBS, whatever the temperature. However, such a concentration is not interesting from an industrial point of view. Indeed, a low concentration requires the distillation of a larger quantity of water, which increases the energy consumption and reduces the productivity and the profitability of the purification method.

In conventional purification methods, at least one polymerisation inhibitor is conventionally used in order to avoid a risk of polymerisation of the monomers during their purification. The method of the invention can reduce the amount of the polymerisation inhibitor(s), or even dispense with them. Indeed, since said polymerisation inhibitors can have a negative effect during the polymerisation, it is advantageous to be able to reduce their quantity.

When the aqueous solution comprises at least one polymerisation inhibitor, the latter is advantageously chosen from, for example and in a non-limiting manner, phenothiazine, (2,2,6,6-tetramethylpiperidin-1-yl)oxyl, 4-hydroxy-2,2,6,6-tetramethylpiperidin-1-oxyl, phenylene diamine derivatives, and their mixtures. Preferably, the polymerisation inhibitor is 4-hydroxy-2,2,6,6-tetramethylpiperidin-1-oxyl.

The polymerisation inhibitors may also be of the phenolic derivative type, such as hydroquinone or paramethoxyphenol, although they function less well than the polymerisation inhibitors described above. Indeed, these inhibitors of phenolic derivative type require dissolved oxygen in the solution in order to effectively play their role as polymerisation inhibitor. Since the aqueous solution of acrylamido-2-methyl-2-propanesulphonic acid is continuously distilled at a pressure below atmospheric pressure, there is less dissolved oxygen to ensure the proper functioning of these inhibitors. When the method according to the invention comprises at least one polymerisation inhibitor, it is preferably not chosen from inhibitors of phenolic derivative type.

The polymerisation inhibitor can already be present in acrylamido-2-methyl-2-propanesulphonic acid or in the aqueous solution of acrylamido-2-methyl-2-propanesulphonic acid, or it can be added at the time of the formation of said aqueous solution, for example by dissolution, or it can also be added continuously during the distillation step.

When the aqueous solution of acrylamido-2-methyl-2-propanesulphonic acid contains a polymerisation inhibitor, its amount is generally less than 1%, preferably less than 0.1%, more preferably less than 0.01%, and even more preferably less than 0.001%, by mass relative to the amount of acrylamido-2-methyl-2-propanesulphonic acid. Preferably, the aqueous solution of acrylamido-2-methyl-2-propanesulphonic acid does not comprise a polymerisation inhibitor.

Conventionally, the recrystallisation of acrylamido-2-methyl-2-propanesulphonic acid requires a hot dissolution step in order to have a saturated solution and to force the crystallisation during a slow step for cooling said solution. These steps consume a lot of energy.

In a preferred embodiment, the method according to the invention does not require a hot dissolution step followed by a slow cooling step.

The preparation of the aqueous solution of acrylamido-2-methyl-2-propanesulphonic acid may be carried out discontinuously (in a batch) or continuously. Preferably it is carried out continuously.

Step 1)—Distillation of the Aqueous Solution of acrylamido-2-methyl-2-propanesulphonic Acid The method according to the invention comprises a step of continuous distillation of the aqueous solution of acrylamido-2-methyl-2-propanesulphonic acid provided as it is or else prepared in the pre-step described above.

The distillation step 1) according to the invention is carried out continuously and at a pressure below atmospheric pressure, generally in a vacuum distillation device, which is typically an evaporator. It is therefore also referred to here as "vacuum distillation".

The term "continuous method" according to the invention is understood to mean a method in which at least one flow enters continuously, advantageously into a vacuum distillation device, and from which at least one flow leaves without interruption. The continuous method according to the invention can operate for several days, or even several months without interruption.

However, it is possible for the continuous method according to the invention to be interrupted exceptionally and then restarted for various reasons. By way of example and in a non-limiting manner, mention may be made of a maintenance operation, or a technical problem. The method is still considered continuous, as opposed to a batch or semi-batch process which is carried out with at least one shutdown between each batch.

When the solution of acrylamido-2-methyl-2-propanesulphonic acid is distilled, typically by passage through an evaporator, crystals of acrylamido-2-methyl-2-propanesulphonic acid begin to form. There is then coexistence of the aqueous solution of acrylamido-2-methyl-2-propanesulphonic acid on which the distillation is carried out and solid particles of acrylamido-2-methyl-2-propanesulphonic acid.

The vacuum distillation can be carried out using an evaporator. It may be a falling film evaporator, or a rising film evaporator, or a scraped thin film evaporator, or a short path evaporator, or a forced circulation evaporator, or a spiral tube evaporator, or even an evaporator by flash cooling. It may also be a continuous stirred reactor. Preferably, the distillation is carried out in a scraped thin film evaporator, or a short path evaporator, or a forced circulation evaporator. Even more preferably, the distillation is carried out in a scraped thin film evaporator.

In general, an evaporator is a device comprising an inlet for the solution to be treated (aqueous solution of ATBS), an outlet for discharging the water and any distilled solvent(s) and an outlet for discharging the concentrated solution (or suspension in the presence of crystals and/or particles). The term "X and/or Y" is understood to mean, according to the invention, either X, or Y, or X and Y.

The residence time of the aqueous solution of acrylamido-2-methyl-2-propanesulphonic acid in the distillation device, which is advantageously an evaporator, in other words the distillation time, is advantageously between 1 second and 600 seconds, preferably between 3 seconds and 300 seconds, more preferably between 30 seconds and 100 seconds. The residence time corresponds to the time necessary for carrying out step 1), i.e. to the time for the preparation of the suspension of ATBS crystals by distillation of the aqueous solution of ATBS. In other words, in the case of an evaporator, this is the residence time of the ATBS, between the inlet and the outlet of the device.

The distillation can be carried out in a vertical or horizontal evaporator. Preferably, it is carried out in a vertical evaporator.

The aqueous solution of acrylamido-2-methyl-2-propanesulphonic acid can circulate in a co-current or counter-current relative to the steam generated by the evaporation. Preferably, it circulates in counter-current to the steam in the distillation device. In other words, the aqueous solution of ATBS is introduced into the distillation device, advantageously an evaporator, co-current or counter-current relative to the distilled solvent.

The aqueous solution of acrylamido-2-methyl-2-propanesulphonic acid may circulate in one or more evaporators in series. Preferably, it circulates in a single evaporator.

According to the method of the invention, with reference to FIG. 1, the flow entering the distillation device of step 1) is flow 1 which corresponds to the aqueous solution of acrylamido-2-methyl-2-propanesulphonic acid supplied or prepared in the pre-step.

The flow rate of the incoming flow 1 is advantageously comprised between 100 kg/h and 200000 kg/h, more advantageously comprised between 200 and 100000 kg/h.

The outgoing flows from the distillation device of step 1) are flow 2, which corresponds to a suspension of acrylamido-2-methyl-2-propanesulphonic acid crystals obtained after vacuum distillation of flow 1, and flow 3, which corresponds to the solvent distilled during distillation. The mass ratio between the flow 2 and the flow 3 generally lies in the range 0.01 to 200, preferably in the range 0.1 to 10, and more preferably in the range 1 to 5.

In flow 2, the proportion of acrylamido-2-methyl-2-propanesulphonic acid in solid (crystals) and liquid (solubilised) form generally represents between 50% and 95% by mass, preferably between 60% and 80% relative to the total mass of flow 2. The rest of the components of the flow 2 are mainly water and potentially another solvent(s).

The flow 3 mainly contains water and may contain a minor amount of one or more other solvent(s), or acrylamido-2-methyl-2-propanesulphonic acid.

The evaporation rate depends on the flow rate of the incoming flow and on the contact surface between the incoming fluid and the distillation device, on the temperature of a heat transfer fluid most often used in connection with the distillation device, and finally on the pressure in the evaporator. The contact surface is dependent on the size of the distillation device; it is defined as being the internal surface of the distillation device in contact with the aqueous solution of acrylamido-2-methyl-2-propanesulphonic acid and/or with the suspension of acrylamido-2-methyl-2-propanesulphonic acid formed inside the distillation device during distillation step 1).

The evaporation rate is calculated as follows:

$$\text{Evaporation rate}(kg/h/m^2) = \text{flow rate } 3(kg/h)/\text{surface of the distillation device}(m^2)$$

The evaporation rate is advantageously comprised between 10 kg/h/m$^2$ and 4000 kg/h/m$^2$, preferably between 20 and 1000 kg/h/m$^2$, even more preferably between 30 and 100 kg/h/m$^2$.

To facilitate the evaporation of the solvent, the distillation may be carried out hot. Heating during distillation can be achieved through various technologies. By way of example and in a non-limiting manner, mention may be made of heating with steam, with hot water, with electricity, by steam compression, or by using a heat pump. Thus, the distillation device can be of the double-walled type, with a hot heat-transfer fluid circulating between the two walls.

The temperature of the inner wall of the distillation device is advantageously comprised between 5 and 90° C., preferably between 30 and 80° C.

The temperature of the aqueous solution of distilled acrylamido-2-methyl-2-propanesulphonic acid (i.e. inside the distillation device) is generally comprised between 5 and 90° C., preferably between 25 and 70° C.

The pressure during distillation is advantageous comprised between 1 and less than 1000 mbar absolute (1 mbar=100 Pa). It is preferably less than 900 mbar absolute, more preferably less than 800 mbar absolute, more preferably less than 700 mbar absolute, more preferably less than 600 mbar absolute, more preferably less than 500 mbar absolute, more preferably less than 400 mbar absolute, more preferably less than 300 mbar absolute, more preferably less than 200 mbar absolute, more preferably less than 100 mbar absolute and even more preferably less than 50 mbar absolute, and advantageously greater than 1 mbar absolute. The absolute pressure corresponds to the pressure relative to zero pressure (vacuum).

The pH of the aqueous solution on which the distillation is carried out is generally and preferably less than 2. Preferably, the vacuum distillation is carried out on the acid form of the acrylamido-2-methyl-2-propanesulphonic acid monomers and not on the partially or completely neutralised form of said monomers.

According to another particular embodiment of the invention, the flow 2 can be cooled before the solid/liquid separation step 2) of the suspension of acrylamido-2-methyl-2-propanesulphonic acid. This has the effect of increasing the productivity and the profitability of the method of the invention by accelerating the crystallisation of acrylamido-2-methyl-2-propanesulphonic acid.

The flow 2 may be cooled using, for example and in a non-limiting manner, a heat exchanger.

According to a particular embodiment of the invention, illustrated in FIG. 1, the flow 3 can be recycled partially or totally in the pre-step if such a pre-step is present, with or without a prior treatment step. In other words, the distilled solvent from step 2) is recycled at least partially into the aqueous solution, generally either in the pre-step, or by mixing with said aqueous solution before step 1).

According to another particular embodiment of the invention, illustrated in FIG. 1, the flow 3 may be partially or totally recycled, generally to wash the acrylamido-2-methyl-2-propanesulphonic acid crystals obtained after the liquid/solid separation step 2), with and/or without a prior treatment step.

According to another particular embodiment of the invention, illustrated in FIG. 1, the flow 3 can be used partially or totally to prepare a salt of acrylamido-2-methyl-2-propanesulphonic acid, with or without a prior treatment step. This salt is then generally used for the synthesis of polymers.

Step 2)—Solid/Liquid Separation of the Suspension of acrylamido-2-méthyl-2-propanesulphonic Acid Obtained after Distillation The crystals of acrylamido-2-methyl-2-propanesulphonic acid are preferably isolated by a liquid/solid separation step from the flow 2, most often leading to the production, in the form of a cake, of crystals of acrylamido-2-methyl-2-propanesulphonic acid. This step is carried out, by way of example and in a non-limiting manner, by means of a horizontal or vertical centrifuge, a decanter, a press filter, a belt filter, a disc filter, a vacuum-closed filter, a pressure-closed filter or a rotary drum filter. Preferably, the liquid/solid separation is carried out using a centrifuge or a closed filter of the Nutsche type.

The aqueous solution recovered after liquid/solid separation step 2) mainly contains water and solubilised acrylamido-2-methyl-2-propanesulphonic acid, and may contain a minor amount of other solvent(s) or impurity(ies).

According to one particular embodiment of the invention, illustrated in FIG. 1, the aqueous solution recovered after the liquid/solid separation can be recycled partially or totally in the pre-step if such a pre-step is present, with or without a prior treatment step.

According to one particular embodiment of the invention, illustrated in FIG. 1, the aqueous solution recovered after the liquid/solid separation can be recycled partially or totally in step 1), with or without a prior treatment step, directly into the distillation device or added to the aqueous solution of acrylamido-2-methyl-2-propanesulphonic acid.

According to another particular embodiment of the invention, illustrated in FIG. 1, the aqueous solution recovered after the liquid/solid separation can be partially or totally recycled in order to prepare a salt of acrylamido-2-methyl-2-propanesulphonic acid, with or without a prior treatment step.

Liquid/solid separation may be carried out discontinuously (in batches) or continuously. Preferably, it is carried out continuously.

Acrylamido-2-methyl-2-propanesulphonic Acid Crystal Washing (Optional)

During an optional washing step illustrated in FIG. 1, the crystals of acrylamido-2-methyl-2-propanesulphonic acid obtained in solid/liquid separation step 2) can be washed using at least one washing solution.

The washing solution mainly comprises water. It can however comprise other solvent(s), as well as dissolved acrylamido-2-methyl-2-propanesulphonic acid.

Advantageously, the washing solution contains no more than 20% by mass of solvent(s) other than water relative to the total mass of the washing solution, preferably less than 15% by mass, more preferably less than 10% by mass, even more preferably less than 8% by mass, even more preferably less than 5% by mass, and even more preferably less than 1% by mass.

According to a particular embodiment of the invention, the crystals obtained from the vacuum distillation can be washed by spraying said crystals with washing solution.

According to another particular embodiment of the invention, the washing of the crystals obtained from the vacuum distillation can be carried out by suspending the crystals in the washing solution.

According to another particular embodiment of the invention, illustrated in FIG. 1, the washing solution is, partially or totally, the distilled phase obtained in step 1) corresponding to the flow 3.

The mass ratio between the washing solution and the crystals of acrylamido-2-methyl-2-propanesulphonic acid obtained from the vacuum distillation is advantageously between 0.1:1 and 10:1 (washing solution/crystals), more preferably between 0.2:1 and 5:1.

The crystals of acrylamido-2-methyl-2-propanesulphonic acid obtained from this washing step are advantageously isolated from the washing solution, for example, by a second optional liquid/solid separation step illustrated in FIG. 1.

The crystals obtained after this second solid/liquid separation step may be used as such or else dried.

However, preferably, the crystals of acrylamido-2-methyl-2-propanesulphonic acid are not dried after the second liquid/solid separation step.

The washing solution recovered after the second liquid/solid separation step contains mainly water and solubilised acrylamido-2-methyl-2-propanesulphonic acid and may contain a minor amount of at least one organic solvent.

According to one particular embodiment of the invention, illustrated in FIG. 1, the washing solution recovered after the second liquid/solid separation step can be recycled partially or totally into the pre-step if such a pre-step exists, with or without a prior treatment step.

According to a particular embodiment of the invention, illustrated in FIG. 1, the washing solution recovered after the second liquid/solid separation step can be recycled partially or totally in step 1), with or without a prior treatment step.

According to another particular embodiment of the invention, illustrated in FIG. 1, the washing solution recovered after the second liquid/solid separation step can be partially or totally recycled in order to prepare an acrylamido-2-methyl-2-propanesulphonic acid salt, with or without a prior treatment step.

According to another particular embodiment of the invention, illustrated in FIG. 1, the washing solution recovered after the second liquid/solid separation step can be partially or totally recycled in order to wash the acrylamido-2-methyl-2-propanesulphonic acid crystals obtained after distillation, with or without a prior treatment step.

The washing operation may be carried out discontinuously (in batches) or continuously. Preferably, it is carried out continuously.

The washing operation may be carried out several times successively if the purity of the crystals of acrylamido-2-methyl-2-propanesulphonic acid is not sufficient.

Drying of acrylamido-2-methyl-2-propanesulphonic Acid Crystals (Optional)

In an optional step, illustrated in FIG. 1, the acrylamido-2-methyl-2-propanesulphonic acid crystals obtained after the solid/liquid separation step 2) or alternatively obtained after the crystal washing step, may be used as such or alternatively dried. By way of example and in a non-limiting manner, drying may be carried out by any drying technology, whether it be by convection, by conduction or by radiation (fluidised-bed drying, through-bed drying, drying on a conveyor belt, microwave drying, high-frequency radiation drying, infrared drying, spray drying, etc.).

The optional drying step may be carried out at atmospheric pressure or else under vacuum.

The optional drying step may be carried out discontinuously (in batch) or continuously. Preferably, it is carried out continuously.

After the liquid/solid separation step 2) or the second liquid/solid separation step, the acrylamido-2-methyl-2-propanesulphonic acid crystals are however preferably not dried.

In a particular embodiment of the invention, it is possible to carry out the washing and drying steps successively.

The method according to the invention makes it possible to obtain crystals of acrylamido-2-methyl-2-propanesulphonic acid of very high purity. The acrylamido-2-methyl-2-propanesulphonic acid crystals thus isolated generally have a degree of purity of between 99.90 and 99.99%, preferably greater than 99.95.

Another advantage of the method according to the invention is the obtaining of acrylamido-2-methyl-2-propanesulphonic acid crystals having a very low level of impurities, typically of the 2-methyl-2-propenyl-sulphonic acid (IBSA) and 2-methylidene-1,3-propylenedisulphonic acid (IBDSA) type, i.e. a small amount of these impurities with respect to the amount by weight of ATBS obtained, these impurities being able to strongly affect the polymerisation beyond a certain concentration. Generally, the crystals obtained according to the invention have an IBSA and IBDSA content of less than 100 ppm by weight, preferably an amount of less than 50 ppm, still more preferably an amount of less than 20 ppm per compound. The other impurities commonly found during the synthesis of ATBS are tert-butylacrylamide, acrylamide and acrylonitrile.

The purity and the amounts of IBDSA and IBSA in the crystals of 2-acrylamido-2-methylpropanesulphonic acid can be measured by HPLC (high performance liquid chromatography) under the following conditions:

Column ODS-3 (GL Science®);
Mobile phase: water with 0.03% trifluoroacetic acid/acetonitrile (mass ratio 90/10);
Mobile phase flow rate: 0.8 ml/minute;
Detection wavelength: 200 nm.

The acrylamido-2-methyl-2-propanesulphonic acid obtained may be in the form of a fine powder or shaped in a controlled manner by a method such as compaction, or granulation, or extrusion.

The acrylamido-2-methyl-2-propanesulphonic acid crystals obtained by the method according to the invention can be redissolved and circulated again in the process according to the invention in order to improve their purity.

Preparation of a Salt or a Solution of Salts of acrylamido-2-methyl-2-propanesulphonic Acid (Optional)

Another aspect of the invention comprises the use of the crystals of acrylamido-2-methyl-2-propanesulphonic acid obtained according to the method of the invention for the production of an aqueous solution of acrylamido-2-methyl-2-propanesulphonate salts.

The acrylamido-2-methyl-2-propanesulphonate salts are obtained by contacting and mixing an aqueous solution of acrylamido-2-methyl-2-propanesulphonic acid with at least one neutralising compound chosen from alkali metal or alkaline-earth metal hydroxides, alkali metal or alkaline-earth metal oxides, ammonia, amines of the following formula $NR_1R_2R_3$ or alkali metal or alkaline-earth metal carbonates.

When the compound is an alkali metal or alkaline earth metal hydroxide, it may be chosen from sodium hydroxide, potassium hydroxide, lithium hydroxide, magnesium hydroxide and calcium hydroxide.

When the compound is an alkaline earth metal oxide, it may be chosen from calcium oxide and magnesium oxide.

When the compound is an amine of formula $NR_1R_2R_3$, $R_1$, $R_2$ and $R_3$ are independently a hydrogen atom or a carbon chain containing from 1 to 22 carbons, advantageously a linear chain, $R_1$, $R_2$ and $R_3$ not being simultaneously a hydrogen atom. In general, ammonia ($NH_3$) is preferred to amines of formula $NR_1R_2R_3$.

It is possible to introduce at least one polymerisation inhibitor during the method for the preparation of acrylamido-2-methyl-2-propanesulphonic acid salt. This inhibitor may be chosen, in a non-limiting manner, from hydroquinone, paramethoxyphenol, phenothiazine, 2,2,6,6-tetramethyl(piperidin-1-yl)oxyl, 4-hydroxy-2,2,6,6-tetramethylpiperidin-1-oxyl, phenylene diamine derivatives, or their mixtures.

Preferably, the inhibitor is paramethoxyphenol.

Acrylamido-2-methyl-2-propanesulphonic Acid Polymers

The invention also relates to a polymer obtained from acrylamido-2-methyl-2-propanesulphonic acid crystals or its salts, obtained according to the method of the invention.

According to another particular embodiment of the invention, the polymer is a copolymer comprising acrylamido-2-methyl-2-propanesulphonic acid obtained according to the method of the invention, and at least one water-soluble monomer.

A (co)polymer denotes a homopolymer of ATBS (acidic and/or salified form) or a copolymer of ATBS (acidic and/or salified form) and at least one other type of monomer.

The water-soluble monomer may be a non-ionic monomer which may in particular be chosen from the group comprising water-soluble vinyl monomers, and in particular acrylamide; N-isopropylacrylamide; N, N-dimethylacrylamide; N-vinylformamide; acryloylmorpholine; N, N-diethylacrylamide; N-tert-butylacrylamide; N-tert-octylacrylamide; N-vinylpyrrolidone; N-vinylcaprolactam; and N-vinylimidazole, hydroxyethylmethacrylamide, hydroxypropylacrylate, isoprenol and diacetoneacrylamide. Advantageously, the non-ionic monomer is acrylamide.

The water-soluble monomer may also be chosen from the group of anionic monomers. The anionic monomer(s) that may be used in the scope of the invention may be chosen from a broad group. These monomers may have vinyl functions, in particular acrylic, maleic, fumaric, malonic, itaconic or allylic functions. They may also contain a carboxylate, phosphonate, phosphate, sulphate or sulphonate group, or some other group having an anionic charge. The anionic monomer may be in acid form or else in the form of an alkaline earth metal salt, an alkali metal salt or an ammonium salt. Examples of suitable monomers include acrylic acid, methacrylic acid, itaconic acid, crotonic acid, maleic acid, fumaric acid, and monomers of the strong acid type having, for example, a function of the sulphonic acid or phosphonic acid type, such as 2-acrylamido 2-methylpropanesulphonic acid, vinylsulphonic acid, vinylphosphonic acid, allylsulphonic acid, allylphosphonic acid, styrene sulphonic acid, and alkali metal, alkaline earth metal, and ammonium salts of these monomers that are soluble in water.

The water-soluble monomer may be a cationic monomer of the acrylamide, acrylic, vinyl, allylic or maleic type having an amine or quaternary ammonium function. Mention may be made, in particular and in non-limiting manner, of quaternised dimethylaminoethyl acrylate (DMAEA), quaternised dimethylaminoethyl methacrylate (DMAEMA), diallyldimethylammonium chloride (DADMAC), acrylamido propyltrimethyl ammonium chloride (APTAC), and methacrylamido propyltrimethyl ammonium chloride (MAPTAC).

The water-soluble monomer may be a zwitterionic monomer such as derivatives having an acrylamide, acrylic, vinyl, allylic or maleic unit, and having an amine or quaternary ammonium function and an acid function of the carboxylic (or carboxylate), sulphonic (or sulphonate) or phosphoric (or phosphate) type. Mention may be made, in particular and in a non-limiting manner, of dimethylaminoethyl acrylate derivatives, such as 2-((2-(acryloyloxy)ethyl) dimethylammonio) dimethylammonio) ethane-1-sulphonate, 3-((2-(acryloyloxy)ethyl) dimethylammonio) propane-1-sulphonate, 4-((2-(acryloyloxy)ethyl) dimethylammonio) butane-1-sulphonate, [2-(acryloyloxy)ethyl] (dimethylammonio) acetate, dimethylaminoethyl methacrylate derivatives, such as 2-((2-(methacryloyloxy) ethyl) dimethylammonio) ethane-1-sulphonate, 3-((2-(methacryloyloxy) ethyl) dimethylammonio) propane-1-sulphonate, 4-((2-(methacryloyloxy) ethyl) dimethylammonio) butane-1-sulphonate, [2-(methacryloyloxy)ethyl](dimethylammonio) acetate, dimethylamino propylacrylamide derivatives, such as 2-(3-(3-acryloyloxy) ethyl) dimethylammonio) dimethylammonio) ethane-1-sulphonate, 3-(3-(3-(methacryloyloxy) dimethylamidopropyl) dimethylammonio) propane-1-sulphonate, 4-(3-(methacryloyloxy) ethyl] (dimethylammonio) propylammonio) acetate, and 3-(3-(dimethylamethylammonoyloxy) dimethylammonio) acetate, such as 2-(3-(3-(3-(methacryloyloxy) ethyl) dimethylammonio) dimethylammonio) butane-1-sulphonate, and 3-(dimethylammonio) propylmethylammonio) acetate.

According to the invention, the (co)polymer may have a linear, branched, crosslinked, star-shaped or comb-shaped structure. These structures can be obtained by selecting the initiator, the transfer agent, the polymerisation technique such as the controlled radical polymerisation called raft (Reversible Addition Chain Transfer), NMP (Nitroxide Mediated Polymerisation) or ATRP (Atom Radical Transfer Polymerisation), of the incorporation of structural monomers, of the concentration.

In general, preparation of the polymer complex of the invention does not require any particular polymerisation method development. Indeed, this complex can be obtained using any of the polymerisation techniques that are well known to a person skilled in the art. In particular, the polymerisation may be solution polymerisation, gel polymerisation, precipitation polymerisation, (aqueous or inverse) emulsion polymerisation, suspension polymerisation, or micellar polymerisation.

According to one particular embodiment of the invention, the (co)polymer may be post-hydrolysed. Post-hydrolysis is the hydrolysis reaction of the (co)polymer after polymerisation. This step consists of reacting the hydrolysable functional groups of the non-ionic monomers, such as the amide or ester functions, with a base. During this step of post-hydrolysis of the copolymer, the number of carboxylic acid functional groups increases. Indeed, the reaction between the base and the amide or ester functions present in the copolymer produces carboxylate groups.

The (co)polymer may be in liquid, gel or solid form when its preparation includes a drying step such as spray drying, spray granulation, drum drying, drying by electromagnetic radiation (microwave, high frequency) or drying in a fluidised bed.

The (co)polymer may have a molecular weight of between 10,000 and 30 million Daltons. It may be a dispersant, a flocculant or a superabsorbent.

The (co)polymer preferably contains at least 1 mol % of acrylamido-2-methyl-2-propanesulphonic acid obtained according to the method of the invention, more preferably at least 5 mol %, even more preferably at least 10 mol %, even more preferably at least 30 mol %, and even more preferably at least 50 mol %.

The invention also relates to the use of the polymer obtained from crystals of acrylamido-2-methyl-2-propanesulphonic acid and/or its salts, obtained according to the method of the invention, in the recovery of oil and gas, in the treatment of water, in the treatment of sludge, in the manufacture of paper, in construction, in the mining industry, in the formulation of cosmetics, in the formulation of detergents, in the manufacture of textiles, or in agriculture.

Oil and gas recovery methods are generally treatments of subterranean formations in which a polymer is used to increase the viscosity of the aqueous injection fluid and/or to reduce the level of frictional resistance that occurs when said fluid is injected into a subterranean formation, or alternatively to block a portion of the subterranean formation occasionally or definitively.

These subterranean treatments include, but are not limited to, drilling operations, stimulation treatments such as fracturing operations, completion operations, and the improved method of sweeping oil with a polymer solution.

The invention also aims to use the polymer obtained from acrylamido-2-methyl-2-propanesulphonic acid crystals obtained according to the method of the invention, in particular as flocculant, dispersant, thickening agent, absorbent agent or friction-reducing agent.

The invention and the advantages procured thereby will be better understood upon reading the following examples provided for illustration purposes and not intended to limit the scope of the invention.

EXAMPLES

All the examples were prepared from the same source of acrylamido-2-methyl-2-propanesulphonic acid. 700 kg of granules of acrylamido-2-methyl-2-propanesulphonic acid are dissolved in 500 kg of water continuously in a stirred reactor. This acrylamido-2-methyl-2-propanesulphonic acid has a purity of 99.8% and comprises 300 ppm of IBDSA and 500 ppm of IBSA.

Example 1—Continuous Comparison Against a Batch 1.1—In the scope of the invention, the solution of acrylamido-2-methyl-2-propanesulphonic acid continuously feeds a thin-film vertical evaporator with a contact surface area of one square meter, at a flow rate of 600 kg·h$^{-1}$. The residence time is 34 seconds. The thin film vertical evaporator is heated by water to 80° C. and the distillation pressure is 30 mbar. The evaporative flow rate which was measured was 72 kg/h/m$^2$. The suspension of acrylamido-2-methyl-2-propanesulphonic acid obtained after distillation is then passed continuously through a horizontal perforated basket wringer, having a speed of rotation of 800 revolutions per minute, before being analysed. The purity of the acrylamido-2-methyl-2-propanesulphonic acid crystals obtained is 99.9667% and comprises 44 ppm of IBDSA and 88 ppm of IBSA. The productivity in crystals of acrylamido-2-methyl-2-propanesulphonic acid is measured at 100 kg·h$^{-1}$.

A washing step with a solution of water is carried out on the cake of acrylamido-2-methyl-2-propanesulphonic acid obtained after passing through the horizontal perforated basket dryer. The purity of the acrylamido-2-methyl-2-propanesulphonic acid crystals obtained is 99.9692% and these crystals comprise 36 ppm of IBDSA and 72 ppm of IBSA. The productivity of acrylamido-2-methyl-2-propanesulphonic acid crystals is measured at 80 kg·h$^{-1}$.

1.2—The same solution of acrylamido-2-methyl-2-propanesulphonic acid as that of Example 1.1 was prepared with the addition of a polymerisation inhibitor (340 g of paramethoxyphenol). The distillation of said solution is carried out in a stirred reactor ("batch"). The reactor has a jacket with a contact surface area of 4.6 m$^2$. The jacket was passed through by water at 80° C. The reactor was placed under vacuum with a pressure of 30 mbar·au á 80° C. The evaporative flow rate which was measured was 15 kg/h/m$^2$. After 24 hours, the suspension of acrylamido-2-methyl-2-propanesulphonic acid obtained passes through a horizontal perforated basket wringer having a speed of rotation of 800 revolutions per minute, before being analysed. The purity of the acrylamido-2-methyl-2-propanesulphonic acid crystals obtained is 99.9% and these crystals comprise 233 ppm of IBDSA and 466 ppm of IBSA. The productivity in crystals of acrylamido-2-methyl-2-propanesulphonic acid is measured at 20 kg·h$^{-1}$.

1.3—The same procedure as in Example 1.2 is followed with the exception of the addition of polymerisation inhibitor. After distillation for 24 hours under the conditions described above, the solution of acrylamido-2-methyl-2-propanesulphonic acid is partially gelled. No crystal of acrylamido-2-methyl-2-propanesulphonic acid can be filtered.

1.4—A conventional purification method with dissolution in acetic acid and slow recrystallisation was carried out. 150 g of acrylamido-2-methyl-2-propanesulphonic acid used in the preceding examples are dissolved, with stirring, in 500 g of acetic acid at a temperature of 90° C. The mixture is left with stirring for 1 hour after the end of the dissolution of the crystals. The solution is left to cool for 2 hours at 5° C. below the crystallisation temperature of acrylamido-2-methyl-2-propanesulphonic acid. After a liquid/solid separation, the crystals were dried in an oven for 6 hours.

The results of the various examples 1.1-1.4 are reported in Table 1.

TABLE 1

Results relating to Examples 1.1 to 1.4.

| Examples | Pressure (mbar) | Purity (%) | IBDSA (ppm) | IBSA (ppm) | Productivity (kg · h$^{-1}$) |
|---|---|---|---|---|---|
| Reference ATBS solution | | 99.8 | 300 | 500 | — |
| 1.1 (invention) | 30 | 99.9667 | 44 | 88 | 100 |
| 1.1 with washing (invention) | 30 | 99.9692 | 36 | 72 | 80 |
| 1.2 (comparison, "batch") | 30 | 99.90 | 233 | 466 | 20 |
| 1.3 (comparison, "batch") | — | — | — | — | — |
| 1.4 (comparison) | — | 99.89 | 159 | 298 | 33 |

It may be observed that the method of the invention makes it possible to have a better productivity than that of a conventional "batch" method: the productivity is multiplied by five. This improves the purity of the acrylamido-2-methyl-2-propanesulphonic acid crystals and reduces the proportion of IBDSA and IBSA in these crystals.

With an additional washing step, the quantity of IBDSA and IBSA can be further reduced, while maintaining a productivity multiplied by four compared to that of a "batch" method.

The method of the invention therefore has better performances than those of a "batch" method, even in the absence of a polymerisation inhibitor. As can be seen in Example 1.3, without a polymerisation inhibitor, acrylamido-2-methyl-2-propane acid self-polymerises in the "batch" method, whereas this does not occur in the case of the method according to the invention.

The method of the invention makes it possible to obtain crystals with lower levels of IBDSA and IBSA, a higher purity and a higher productivity compared with a purification method conventionally used for purifying acrylamido-2-methyl-2-propane acid with slow crystallisation in a solvent (Example 1.4).

Example 2—Impact of Pressure

Example 1.1 was reproduced without the washing step, at different pressures (Examples 2.1 to 2.3). The results are summarised in Table 2.

TABLE 2

Results relating to Examples 2.1 to 2.3.

| Examples | Pressure (mbar) | Purity (%) | IBDSA (ppm) | IBSA (ppm) | Productivity (kg · h$^{-1}$) |
|---|---|---|---|---|---|
| Reference ATBS solution | | 99.8 | 300 | 500 | — |
| 2.1 (invention) | 30 | 99.9667 | 44 | 88 | 100 |
| 2.2 (invention) | 60 | 99.9671 | 10 | 20 | 50 |
| 2.3 (invention) | 300 | 99.963 | 22 | 44 | 10 |

It may be observed that pressure plays an important role in the method according to the invention. By increasing the distillation pressure, the productivity decreases, while it is possible to reduce the quantity of IBDSA and residual IBSA. Above 300 mbar, productivity is generally no longer industrially attractive.

A person skilled in the art will be able to adjust the distillation pressure according to whether they are interested in a greater purity of acrylamido-2-methyl-2-propane acid crystals or a greater productivity.

Example 3—Comparison of Solvents

Example 1.1 was reproduced without the washing step, with different solvents (Examples 3.1 to 3.4). The results are summarised in Table 3.

TABLE 3

Results relating to Examples 3.1 to 3.4.

| Examples | Solvent | Purity (%) | IBDSA (ppm) | IBSA (ppm) | Productivity (kg · h$^{-1}$) |
|---|---|---|---|---|---|
| Reference ATBS solution | | 99.8 | 300 | 500 | — |
| 3.1 (invention) | Water | 99.9667 | 44 | 88 | 100 |
| 3.2 (invention) | Acetic acid (25)/water (75) | 99.91 | 154 | 92 | 46 |
| 3.3 (invention) | Acetic acid (8)/water (92) | 99.9658 | 47 | 94 | 76 |
| 3.4 (invention) | Acrylonitrile (10)/water (90) | 99.9572 | 43 | 86 | 82 |

The use of water as solvent makes it possible to obtain crystals of better purity but also crystals containing less IBDSA and IBSA. Productivity is also higher for the method using only water. The invention thus makes it possible to have a more productive method while reducing the environmental footprint, the cost and the risks associated with the use, storage and handling of solvents.

The method according to the invention makes it possible to obtain acrylamido-2-methyl-2-propane acid crystals which can be used for the preparation of acrylamido-2-methyl-2-propane acid salts and of polymers which offer better performances than polymers derived from impurified crystals according to the invention.

The invention claimed is:

1. A method for the purification of acrylamido-2-methyl-2-propanesulphonic acid, comprising the following successive steps:
1) preparing a suspension of acrylamido-2-methyl-2-propanesulphonic acid crystals by distillation of an aqueous solution of acrylamido-2-methyl-2-propanesulphonic acid,
2) isolating the acrylamido-2-methyl-2-propanesulphonic acid crystals by solid/liquid separation of said suspension,
wherein the distillation is carried out continuously and at a pressure below atmospheric pressure, and
wherein the aqueous solution of acrylamido-2-methyl-2-propanesulphonic acid, prior to the distillation, comprises at least 80% by mass of water, based on the total mass of the solvents of the solution.

2. The method according to claim 1, wherein the aqueous solution comprises at least one polymerisation inhibitor and the amount of polymerisation inhibitor, relative to the amount of acrylamido-2-methyl-2-propanesulphonic acid crystals of said aqueous solution, is less than 1% by mass.

3. The method according to claim 1, wherein the distilled solvent resulting from step 1) is recycled at least partially into the aqueous solution.

4. The method according to claim 1, wherein the distillation is carried out in a distillation device which is an evaporator.

5. The method according to claim 4, wherein the aqueous solution of acrylamido-2-methyl-2-propanesulphonic acid is passed in counter-current into the distillation device.

6. The method according to claim 1, wherein the distillation time is comprised between 1 and 600 seconds.

7. The method according to claim 1, wherein the temperature of the distilled acrylamido-2-methyl-2-propanesulphonic acid solution is between 5 and 90° C.

8. The method according to claim 1, wherein the pressure during the distillation is comprised between 1 and less than 1000 mbar absolute.

9. The method according to claim 1, wherein the isolating step 2) is carried out continuously.

10. The method according to claim 1, wherein the crystals of acrylamido-2-methyl-2-propanesulphonic acid obtained after step 2) are washed with at least one washing solution.

11. The method according to claim 1, comprising a drying operation of the acrylamido-2-methyl-2-propanesulphonic acid crystals obtained after the solid/liquid separation step 2) or else obtained after a crystal washing step, optionally followed by a second liquid/solid separation step carried out continuously.

12. The method according to claim 1, wherein the concentration of acrylamido-2-methyl-2-propanesulphonic acid in the aqueous solution of acrylamido-2-methyl-2-propanesulphonic acid distilled in step 1) is comprised between 10% and 58%, by mass, corresponding to the saturation of the solution at 25° C.

13. The method according to claim 2, wherein the aqueous solution comprises at least one polymerisation inhibitor and the amount of polymerisation inhibitor, relative to the amount of acrylamido-2-methyl-2-propanesulphonic acid crystals of said aqueous solution, is less than 1% by mass.

14. The method according to claim 2, wherein the distilled solvent resulting from step 2) is recycled at least partially into the aqueous solution.

15. The method according to claim 14, wherein the distillation is carried out in a distillation device which is an evaporator, preferably a scraped thin film evaporator, or a short path evaporator, or a forced circulation evaporator.

16. The method according to claim 15, wherein the aqueous solution of acrylamido-2-methyl-2-propanesulphonic acid is passed in counter-current into the distillation device.

17. The method according to claim 1, wherein:
the distillation time is comprised between 1 and 600 seconds;
the temperature of the distilled acrylamido-2-methyl-2-propanesulphonic acid solution is between 5 and 90° C.;
the pressure during the distillation is comprised between 1 and less than 1000 mbar absolute; and
the isolating step 2) is carried out continuously.

18. The method according to claim 4, wherein the evaporator is a scraped thin film evaporator, a short path evaporator, or a forced circulation evaporator.

\* \* \* \* \*